United States Patent
Nezhat

[11] Patent Number: 6,030,384
[45] Date of Patent: Feb. 29, 2000

[54] BIPOLAR SURGICAL INSTRUMENTS HAVING FOCUSED ELECTRICAL FIELDS

[76] Inventor: Camran Nezhat, 240 Mountain Wood La., Woodside, Calif. 94062

[21] Appl. No.: 09/071,689
[22] Filed: May 1, 1998
[51] Int. Cl.⁷ .................................................. A61B 17/39
[52] U.S. Cl. .............................................. 606/48; 606/51
[58] Field of Search .................... 606/48, 50–52, 606/45, 49

[56] References Cited

U.S. PATENT DOCUMENTS

| | | |
|---|---|---|
| 3,920,021 | 11/1975 | Hiltebrandt . |
| 4,016,886 | 4/1977 | Doss et al. ................................ 128/422 |
| 4,041,952 | 8/1977 | Morrison, Jr. et al. . |
| 4,043,342 | 8/1977 | Morrison, Jr. . |
| 4,671,274 | 6/1987 | Sorochenko . |
| 5,098,431 | 3/1992 | Rydell . |
| 5,151,102 | 9/1992 | Kamiyama et al. . |
| 5,207,691 | 5/1993 | Nardella . |
| 5,217,030 | 6/1993 | Yoon . |
| 5,217,460 | 6/1993 | Knoepfler ................................... 606/52 |
| 5,267,998 | 12/1993 | Hagen . |
| 5,269,780 | 12/1993 | Roos . |
| 5,269,782 | 12/1993 | Sutter . |
| 5,281,216 | 1/1994 | Klicek . |
| 5,282,799 | 2/1994 | Rydell . |
| 5,290,287 | 3/1994 | Boebel et al. . |
| 5,295,990 | 3/1994 | Levin . |
| 5,300,087 | 4/1994 | Knoepfler . |
| 5,324,289 | 6/1994 | Eggers . |
| 5,330,471 | 7/1994 | Eggers . |
| 5,336,229 | 8/1994 | Noda . |
| 5,342,381 | 8/1994 | Tidemand . |
| 5,352,223 | 10/1994 | McBrayer et al. . |

(List continued on next page.)

FOREIGN PATENT DOCUMENTS

| | | |
|---|---|---|
| 598149 | 7/1925 | France . |
| 197711 | 11/1977 | Russian Federation . |

*Primary Examiner*—Linda C. M. Dvorak
*Assistant Examiner*—Roy Gibson
*Attorney, Agent, or Firm*—Townsend and Townsend and Crew LLP

[57] ABSTRACT

A bipolar surgical device includes a pair of actuable jaws. A first electrode member which usually includes a line of electrically coupled tissue penetrating elements is formed on one of the jaws, and a second electrode member which usually includes a line of electrically coupled tissue penetrating elements is formed on the same or the other jaw. The electrode members are laterally spaced-apart and arranged in a parallel, usually linear manner so that the lateral distance therebetween remains generally constant. In operation, tissue may be grasped between the jaws so that the electrode members contact and/or the tissue penetrating elements enter into the tissue. By energizing the electrode members at opposite polarities using a high frequency energy source, tissue between the jaws will be heated, coagulated, and/or necrosed, while heating of tissue outside of the lines will be minimized.

49 Claims, 6 Drawing Sheets

6,030,384
Page 2

U.S. PATENT DOCUMENTS

| | | |
|---|---|---|
| 5,352,235 | 10/1994 | Koros et al. . |
| 5,356,408 | 10/1994 | Rydell . |
| 5,383,876 | 1/1995 | Nardella . |
| 5,391,166 | 2/1995 | Eggers . |
| 5,395,369 | 3/1995 | McBrayer et al. . |
| 5,396,900 | 3/1995 | Slater et al. . |
| 5,403,312 | 4/1995 | Yates et al. . |
| 5,417,687 | 5/1995 | Nardella et al. . |
| 5,423,814 | 6/1995 | Zhu et al. . |
| 5,443,463 | 8/1995 | Stern et al. . |
| 5,445,638 | 8/1995 | Rydell et al. . |
| 5,456,684 | 10/1995 | Schmidt et al. . |
| 5,458,598 | 10/1995 | Feinberg et al. . |
| 5,462,546 | 10/1995 | Rydell . |
| 5,469,312 | 11/1995 | Klicek . |
| 5,482,054 | 1/1996 | Slater et al. . |
| 5,484,435 | 1/1996 | Fleenor et al. . |
| 5,484,436 | 1/1996 | Eggers et al. . |
| 5,496,317 | 3/1996 | Goble et al. . |
| 5,514,134 | 5/1996 | Rydell et al. . |
| 5,527,313 | 6/1996 | Scott et al. ........................... 606/51 |
| 5,531,744 | 7/1996 | Nardella et al. . |
| 5,540,684 | 7/1996 | Hassler, Jr. . |
| 5,540,685 | 7/1996 | Parins et al. . |
| 5,542,945 | 8/1996 | Fritzsch . |
| 5,549,606 | 8/1996 | McBrayer et al. . |
| 5,558,100 | 9/1996 | Cox . |
| 5,558,671 | 9/1996 | Yates . |
| 5,569,243 | 10/1996 | Kortenbach et al. . |
| 5,573,535 | 11/1996 | Viklund . |
| 5,578,052 | 11/1996 | Koros et al. . |
| 5,599,350 | 2/1997 | Schulze et al. . |
| 5,603,711 | 2/1997 | Parins et al. . |
| 5,624,452 | 4/1997 | Yates . |
| 5,626,578 | 5/1997 | Tihon . |
| 5,637,110 | 6/1997 | Pennybacker et al. . |
| 5,637,111 | 6/1997 | Sutcu et al. . |
| 5,658,281 | 8/1997 | Heard . |
| 5,662,680 | 9/1997 | Desai . |
| 5,665,085 | 9/1997 | Nardella . |
| 5,665,100 | 9/1997 | Yoon . |
| 5,667,526 | 9/1997 | Levin . |
| 5,669,907 | 9/1997 | Platt, Jr. et al. . |
| 5,674,184 | 10/1997 | Hassler, Jr. . |
| 5,674,220 | 10/1997 | Fox et al. . |
| 5,681,282 | 10/1997 | Eggers et al. . |
| 5,683,385 | 11/1997 | Kortenbach et al. . |
| 5,683,388 | 11/1997 | Slater . |
| 5,688,270 | 11/1997 | Yates et al. . |
| 5,693,051 | 12/1997 | Schulze et al. . |
| 5,697,949 | 12/1997 | Giurtino et al. . |
| 5,700,261 | 12/1997 | Brinkerhoff . |
| 5,702,390 | 12/1997 | Austin et al. . |
| 5,707,369 | 1/1998 | Vaitekunas et al. . |
| 5,709,680 | 1/1998 | Yates et al. . |
| 5,713,896 | 2/1998 | Nardella . |
| 5,718,703 | 2/1998 | Chin . |
| 5,733,283 | 3/1998 | Malis et al. . |
| 5,735,848 | 4/1998 | Yates et al. . |
| 5,735,849 | 4/1998 | Baden et al. . |
| 5,741,285 | 4/1998 | McBrayer et al. . |
| 5,743,906 | 4/1998 | Parins et al. . |
| 5,755,717 | 5/1998 | Yates et al. . |
| 5,891,142 | 4/1999 | Eggers et al. ........................... 606/51 |

BIPOLAR SURGICAL INSTRUMENTS HAVING FOCUSED ELECTRICAL FIELDS

BACKGROUND OF THE INVENTION

1. Field of the Invention

The present invention relates generally to medical devices and methods. More particularly, the present invention relates to the structure and use of bipolar forceps and other instruments for coagulating, cutting, and necrosing tissue.

Electrosurgery refers broadly to a class of medical procedures which rely on the application of high frequency electrical energy, usually radio frequency energy, to patient tissue to achieve a number of possible effects, such as cutting, coagulation, hyperthermia, necrosis, and the like. Of particular interest to the present invention, bipolar electrosurgical devices rely on contacting electrodes of different polarity in close proximity to each other against or into tissue. For example, bipolar forceps 100 (FIGS. 1 and 2) have been used for cutting and coagulating tissue, where the opposed jaws 102 and 104 of the forceps are connected to different poles of an electrosurgical power supply. The high frequency electrical current thus flows from one jaw to the other through the tissue present therebetween. Use of such bipolar forceps is effective for a number of purposes and advantageous in that its effect is generally limited to the tissue held between the jaws. Heating, however, is not totally limited to such intermediate tissue, and in some instances heating of adjacent tissues can be problematic. Such heating occurs because the current flows not only between the jaws but also laterally outward, as shown by flux lines F in FIG. 1B.

Various improvements to bipolar forceps have been proposed. For example, the placement of pins or other tissue-penetrating elements onto the tissue-engaging surface(s) of either or both jaws has been suggested for a variety of purposes. Regardless of the intended purpose, the placement of tissue-penetrating elements on the jaw(s) can marginally focus the current density and somewhat lessen heating of adjacent tissues. Such prior designs employing tissue-penetrating elements, however, still cause unwanted heating of adjacent tissues in at least certain circumstances.

A second problem with conventional bipolar forceps is limited power delivery. With conventional forceps, jaws having a length of about 20 mm and a width of about 5 mm can usually deliver only 25 W of current without causing charring of the tissue. Charring greatly increases electrical resistance through the tissue and can result in premature termination of the treatment. With such a low power level, the time to fully coagulate the tissue can be excessive.

It would therefore be desirable to provide still further improved bipolar forceps and other electrosurgical device designs. In particular, it would be desirable to provide bipolar forceps which provide a very high degree of focused heating, i.e., provide heating of tissue between the jaws with minimized heating of tissue adjacent to the jaws. It would be further desirable to provide bipolar forceps which can deliver higher current flows and densities to the tissue being treated without charring the tissue and terminating the current flow. Such device designs should be relatively simple and easy to fabricate. The devices and methods should be compatible with conventional electrosurgical power supplies and usable in a wide variety of procedures, including cutting, coagulation, and necrosis, where the localized and specific heating of patient tissues is desired. At least some of these objectives will be met by the invention described hereinafter.

2. Description of the Background Art

Bipolar forceps having penetrating elements on opposed jaws thereof are described in U.S. Pat. Nos. 5,527,313 and 5,217,460; Soviet Union Patent Publication SU197711; and French Patent No. 598,149. A radio frequency tumor heating device comprising parallel electrode arrays of opposite polarity is described in U.S. Pat. No. 4,016,886.

SUMMARY OF THE INVENTION

The present invention provides improved bipolar surgical instruments, such as forceps, graspers, or the like, which comprise a pair of opposed jaws at the distal end of a shaft. The present invention is directed at a unique electrode configuration on either or both of the jaws which will provide improved current focussing characteristics and lessened heating of adjacent tissues. In particular, electrode members on either or both of the jaws will be laterally spaced apart from each other when the jaws are closed so that current will flow from one electrode to the other with minimum current flow outside of the region defined between the electrodes. optionally, a pair of electrodes can be provided on each jaw with a positive and negative electrode on one jaw and a positive and negative electrode on the other jaw, with the two positive electrodes and the two negative electrodes being aligned with each other when the jaws are closed to defined the desired focussed current flow.

Preferably, at least one of the electrode members will include tissue penetrating elements. Usually a first line of electrically coupled tissue penetrating elements will be provided on a first electrode member, and a second line of electrically coupled tissue penetrating elements will be provided on a second electrode member. Third and fourth lines of electrically coupled tissue penetrating elements will preferably be provided when third and fourth electrode members are provided on the instrument. The first and second lines (and optionally third and fourth lines) of tissue penetrating elements will be electrically isolated from each other to permit energization in a bipolar manner, i.e., each line of electrically coupled tissue penetrating elements may be separately connected to the opposite pole of a conventional electrosurgical power supply. The shaft includes or comprises an actuating mechanism for moving the jaws between opened and closed configurations, where the lines of tissue penetrating elements lie parallel to and spaced-apart from each other when the jaws are closed. In this way, the jaws can be closed on a target tissue structure, such as a fallopian tube, artery, vein, and the like, in order to penetrate the lines of elements into the tissue. By then applying high frequency electrical energy to the lines in a bipolar manner, current flux will be focused to within that portion of the tissue which lies between the adjacent lines, with minimum heating of tissue outside of the parallel lines. Usually, but not necessarily, the lines will both be straight. Alternatively, the lines could be nonlinear, e.g., curved, serpentine, zig-zag, or the like, so long as the patterns are similar and the lateral spacing between adjacent points on the lines remains substantially constant. Preferably, the spacing between the adjacent lines of tissue penetrating elements will be in the range from 0.5 mm to 10 mm, more preferably from 2 mm to 5 mm.

The lines of tissue penetrating elements may be on the same jaw or on different jaws. When the lines are on the same jaw, it is necessary to provide insulation so that each line is electrically isolated from the other, while the plurality of tissue penetrating elements in an individual line remain electrically coupled. Electrical conductors will be provided within the shaft in order to permit attachment of each line to opposite polarity connections on an electrosurgical power supply. When present on different jaws, the lines of tissue penetrating elements may be isolated from each other by maintaining appropriate electrical isolation between the jaws and/or at either or both ends of the tissue penetrating elements.

The tissue penetrating elements may have a wide variety of different configurations. Most commonly, they will be in the form of a pin or other rod-like tissue-penetrating electrode, usually having a sharpened distal end to facilitate penetration into tissue. Alternatively, an appropriate cutting current could be applied to the electrodes in order to facilitate tissue penetration while the jaws are being closed. Each line of tissue penetrating elements may contain from 2 to 50 individual elements, usually from 6 to 10. The elements may extend over a length on the jaw(s) in the range from 1 mm to 10 mm, usually from 2 mm to 5 mm, with spacing between individual elements being in the range from 0.5 mm to 3 mm, usually from 0.5 mm to 2 mm. The height of the tissue penetrating elements (corresponding to the depth of tissue penetration) will usually be in the range from 1 mm to 10 mm, preferably from 2 mm to 5 mm, while the diameter of the elements will typically from 0.1 mm to 10 mm, usually from 0.5 mm to 0.5 mm.

Optionally, either or both of the jaws may be perforated or otherwise provided with passages in order to permit the release of steam which is a byproduct of tissue heating. A mechanism will be provided on the shaft for actuating the jaws, i.e., opening and closing the jaws so that they may grasp tissue therebetween. Exemplary actuating mechanisms include scissors, camming mechanisms, linear/pivot actuators, and the like.

Methods according to the present invention rely on grasping tissue between a first jaw and a second jaw. A high frequency energy is then applied between a first line of tissue penetrating elements on one of the jaws and a second line of tissue penetrating elements on the same or a different jaw. The tissue penetrating element lines are parallel and spaced-apart from each other, generally as described above. The high frequency energy will preferably be applied to the tissue at a level and for a time sufficient to necrose substantially all tissue between the lines without causing substantial damage to other tissue, i.e., tissue outside of the lines. Typically, the high frequency energy will be applied at a frequency in the range from 100 kHz to 1 MHz, preferably from 400 kHz to 500 kHz. The energy will be applied at a power from 25 W to 200 W, preferably from 50 W to 100 W, and for a time in the range from 5 seconds to 5 minutes, usually from 10 seconds to 40 minutes.

DESCRIPTION OF THE SPECIFIC EMBODIMENTS

Figure 1A:
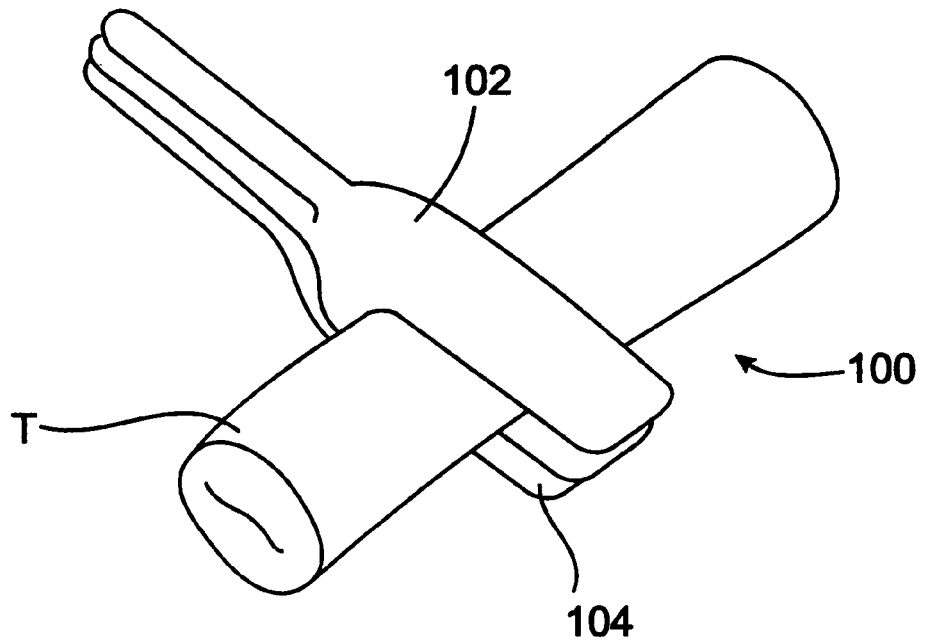
FIGS. 1A and 1B illustrate use of conventional bipolar forceps for coagulating a tubular structure in the body.

According to the present invention, bipolar surgical instruments will include at least two and up to four or more laterally spaced-apart electrode members disposed on a pair of actuable jaws. By properly positioning the electrode members relative to each other, radio frequency energy applied to tissue disposed between the jaws can be focused within a well-defined region between the electrode members. In contrast to prior art devices and methods, where electrodes of opposite polarity are generally engaged against directly opposed tissue surfaces, the present invention will position at least one positive electrode and at least one negative electrode on and/or into laterally spaced-apart sites on opposed tissue surfaces.

The electrode members may be configured in a wide variety of patterns and designs, some of which are illustrated in FIGS. 2A–2E. Most simply, one jaw 200 may carry a first electrode member 202 which is laterally spaced-apart from a second electrode member 204, where the electrode members are connectable to opposite poles of a power supply. An opposed jaw 206 may be free from electrodes of any sort. The jaws 200 and 206 will be actuable, as described in more detail hereinafter, so the tissue may be grasped between two opposed tissue-engaging surfaces 208 and 210. When tissue is grabbed between the jaws 200 and 206, current flow will be generally limited to between the electrode members 202 and 204.

Figure 2A:
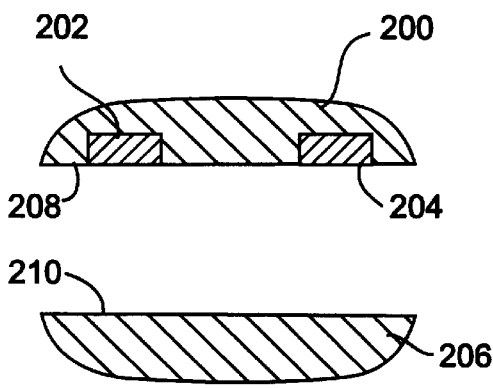
FIGS. 2A–2F illustrate a plurality of alternative electrode configurations according to the method of the present invention.
Figure 2D:
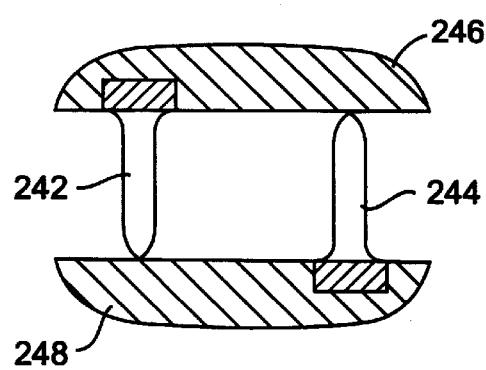
Figure 2B:
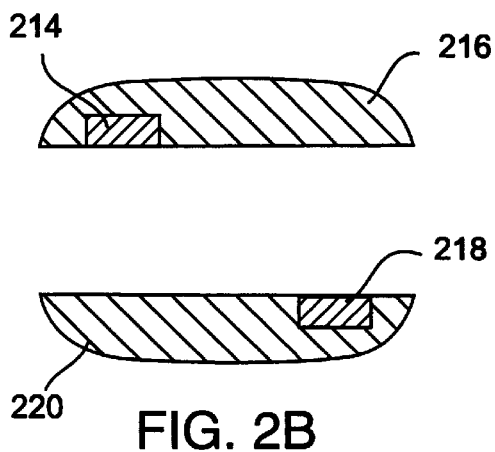

While the electrode member configuration of FIG. 2A is functional, the current flow pattern between the electrodes can be improved by having a first electrode member 214 on a first jaw 216 and a second electrode member 218 on a second jaw 220 as illustrated in FIG. 2B. As with the configuration of FIG. 2A, the electrode members 214 and 218 of FIG. 2B will generally limit current flow so that it does not extend significantly to tissue outside the lateral boundaries of the jaws 216 and 220. By placing the electrode members 214 and 218 on opposed jaws, enhanced current flow through the tissue may be achieved.

Figure 2E:
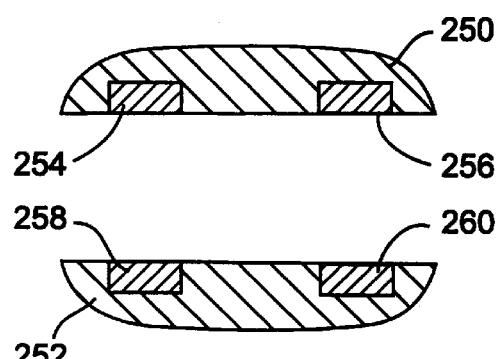
Figure 2C:
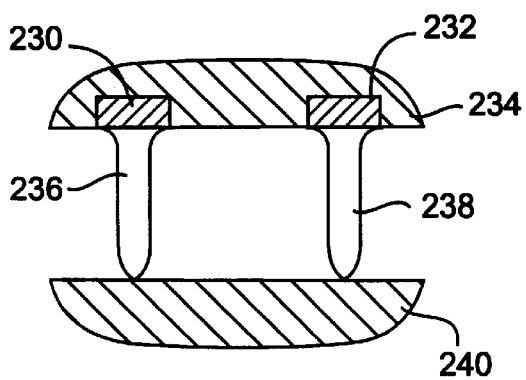

A further alternative improved configuration of the electrode members according to the present invention is illustrated in FIG. 2C. First electrode member 230 and second electrode member 232 are each carried on a first jaw 234, in a manner similar to the embodiment of FIG. 2A. The electrode members 230 and 232, however, each include a line of tissue-penetrating elements thereon. The electrode members 202 and 204 in FIG. 2A are generally linear electrodes having a width and length within the ranges set forth above. Such electrodes will form a flat contact or interface with the tissue which is engaged between the jaws 200 and 206. By providing tissue-penetrating elements 236 and 238, as illustrated in FIG. 2C, two advantages are achieved. First, the total electrode area in contact with the tissue can be greatly enhanced, typically from two-fold to 10-fold, or greater. Moreover, by extending the electrode "boundaries" into the tissue, the ability to achieve uniform current flux within the tissue is improved and the containment of that current flux within the target region is also enhanced. The embodiment of FIG. 2C will include an opposed jaw 240 which is free from electrodes.

A slightly modified configuration for tissue penetrating elements 242 and 244 is illustrated in FIG. 2D. Instead of carrying both lines of tissue penetrating elements 242 and 244 on a single jaw, the first line 242 is carried on an upper jaw 246 and the second line 244 is carried on a lower jaw 248. The advantages regarding increased electrode area and current flux containment, however, are generally comparable to those achieved with the embodiment of FIG. 2C.

Yet another alternative for the electrode member configuration is illustrated in FIG. 2E. Jaws 250 and 252 each carry pairs of laterally spaced-apart members 254, 256, 258 and 260. The electrode members can be adapted for connection to a power supply so that laterally spaced-apart pairs of electrodes will have opposite polarity when the instrument is powered. For example, electrodes 254 and 258 may have a first polarity while electrodes 256 and 260 may have a second polarity. Alternatively, but less preferably, electrodes 254 and 260 may have a first polarity while electrodes 258 and 256 may have a second polarity. The latter configuration will be generally less effective at containing current flow than the former configuration since pairs of oppositely energized electrodes will directly oppose each other when the instrument is engaged against tissue.

Figure 2F:
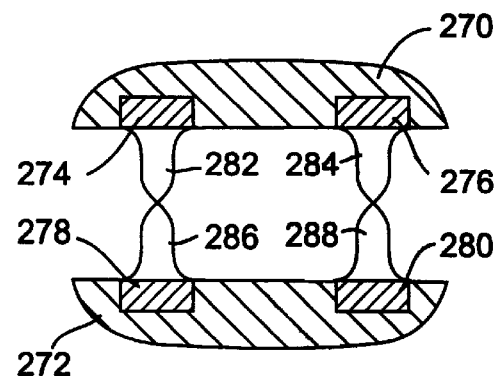

Yet another electrode configuration is illustrated in FIG. 2F. There, each jaw 270 and 272 carries a pair of electrode members 274, 276, 278, 280. Each of the electrode members, in turn, carries a line of tissue-penetrating elements 282, 284, 286, 288. The tissue-penetrating elements are arranged so that their distal tips will engage each other when the jaws 270 and 272 are closed together. Opposed pairs of electrode members 274/278 and 276/280 will have the same polarity, i.e. the laterally spaced-apart pairs will be of opposite polarity. In many ways, the operation of the embodiment of FIG. 2F will be the same as that of both FIG. 2C and FIG. 2D. The embodiment of FIG. 2F may also be modified by axially spacing apart the opposed penetrating elements 282/286 and 284/288 so that the elements penetrate fully to the opposed jaw 270 or 272. A variety of other electrode modifications will also be possible within the scope and spirit of the present invention.

Figure 3A:
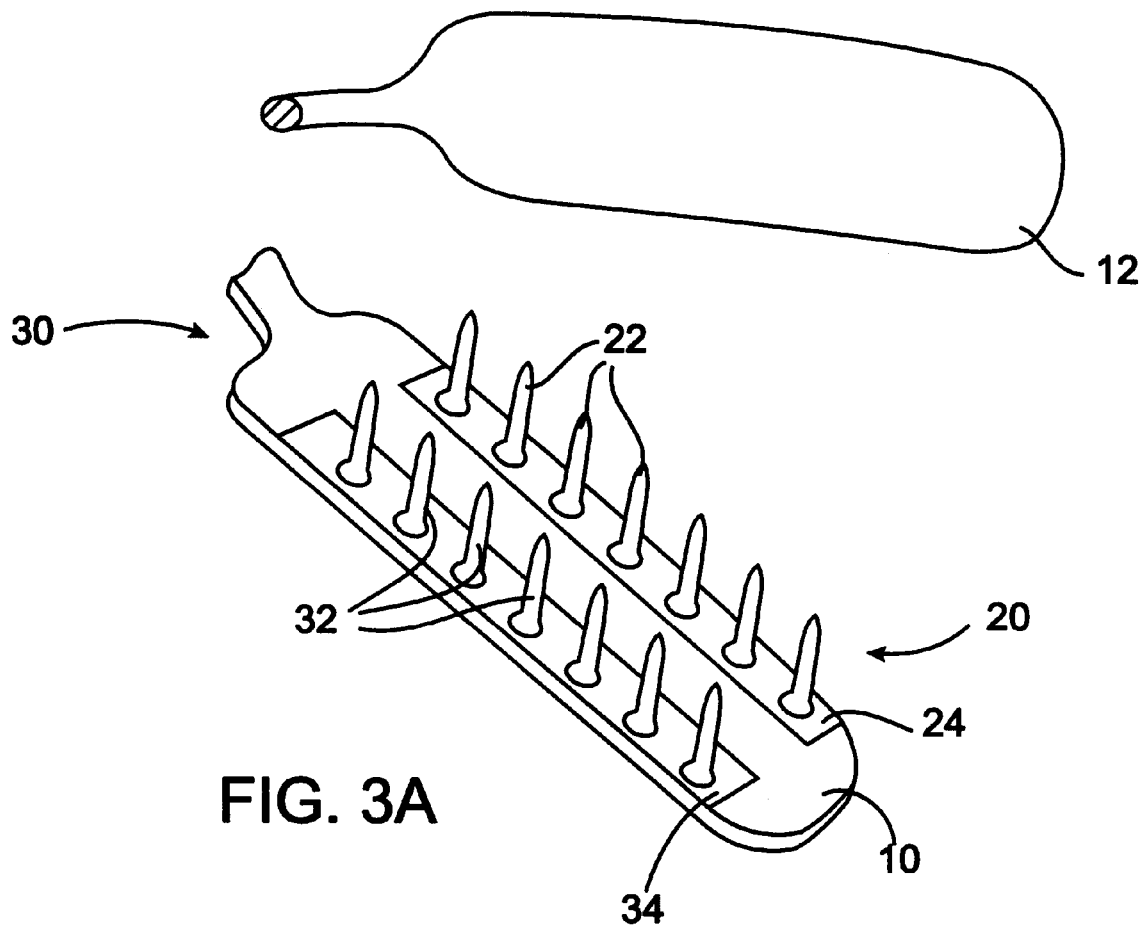
FIG. 3A is a perspective view of a pair of actuable jaws carrying two lines of electrically coupled tissue penetrating elements in accordance with the principles of the present invention.
Figure 3B:
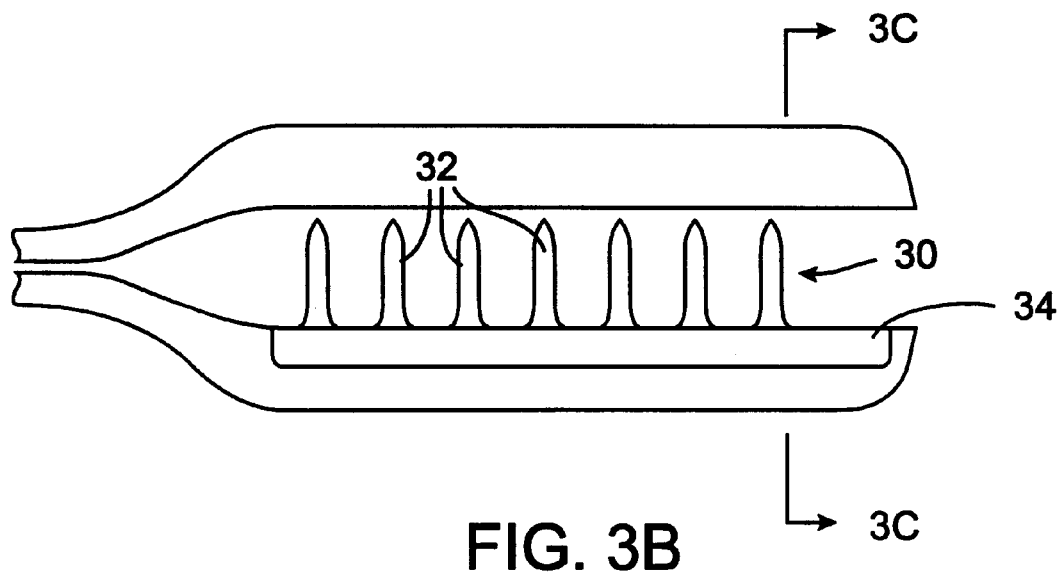
FIG. 3B is a side, elevational view of the jaws of FIG. 1, shown with the jaws closed.
Figure 3C:
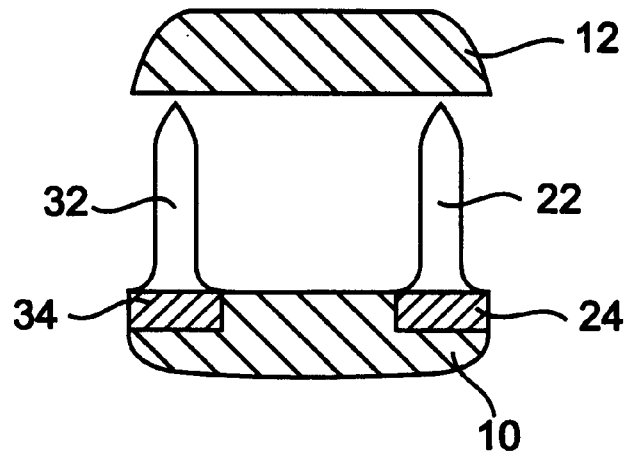
FIG. 3C is a cross-sectional view taken along line 3—3 of FIG. 2.

Referring now to FIGS. 3A–3C, a first exemplary pair of jaws 10 and 12 which may be utilized for grasping tissue and applying high frequency energy according to the methods of the present invention will be described. The jaws 10 and 12 will be actuable or reciprocatable in a manner conventional for forceps, graspers, and other similar types of medical devices. Specific shaft designs which provide for such actuation will be described hereinafter in connection with FIGS. 5–7.

A first line 20 comprising seven tissue penetrating pins 22 is disposed on one side of the lower jaw 10 and a second line 30 of tissue penetrating pins 32 is disposed on the other side of the lower jaw. The first line 20 of pins 22 is electrically coupled by an electrically conductive strip 24 into which the pins are attached. Similarly, a second electrically conductive strip 34 is disposed on the other side of the jaw and electrically couples the second line 30 of pins 32. Each of the electrically conductive strips 24 and 32 will be attached to conductors (not shown) which extend proximally down the shaft of the device and which provide for electrical attachment of the lines 20 and 30 to a conventional electrosurgical power supply.

The electrically conductive strips 24 and 34 will be electrically isolated from each other. For example, the strips 24 and 34 may be imbedded in an insulating material, such as a ceramic, plastic, or the like. Alternatively, an insulating layer may be formed around the strips 24 so that they are electrically isolated from the lower jaw 10. The upper jaw 12 may also be formed from a ceramic or other electrically insulating material to assure that the pins 22 and 32 are not shorted by contact with the upper jaw. The pins 22 and 32 and strips 24 and 34 will be formed from an electrically conductive material, typically a metal such as stainless steel, gold, silver, or the like. The dimensions, number, spacing, and other characteristics of the pins 22 and 32 will be within the ranges set forth above. While shown in a straight line, the pins 22 and 32 could also be arranged in the other patterns set forth above.

Figure 4:
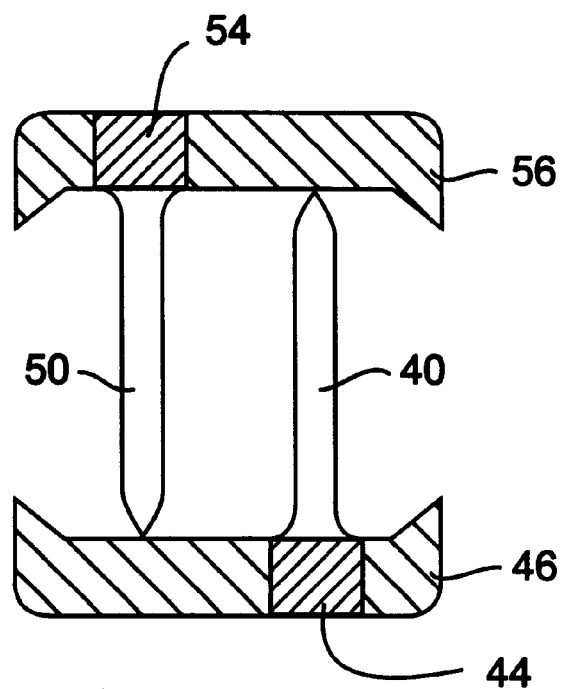
FIG. 4 is an alternative cross-sectional view of a pair of jaws constructed in accordance with the principles of the present invention.

The embodiment of FIGS. 3A–3C shows both lines 20 and 30 of tissue penetrating elements 22 and 32 being connected to the same jaw. The present invention would also cover embodiments where the lines of tissue penetrating elements are connected to opposite jaws, as shown in FIG. 4. There, a first line of pins 40 are mounted within a conductive strip 44 in a lower jaw 46, while a second line of tissue penetrating elements 50 are mounted in an electrically conductive strip 54 in an upper jaw 56. The individual tissue penetrating elements 40 and 50 are thus coupled to each other within each line, but the two lines are electrically isolated, so that the result is a pair of electrically isolated lines of tissue penetrating elements, as with the first embodiment.

Figure 5:
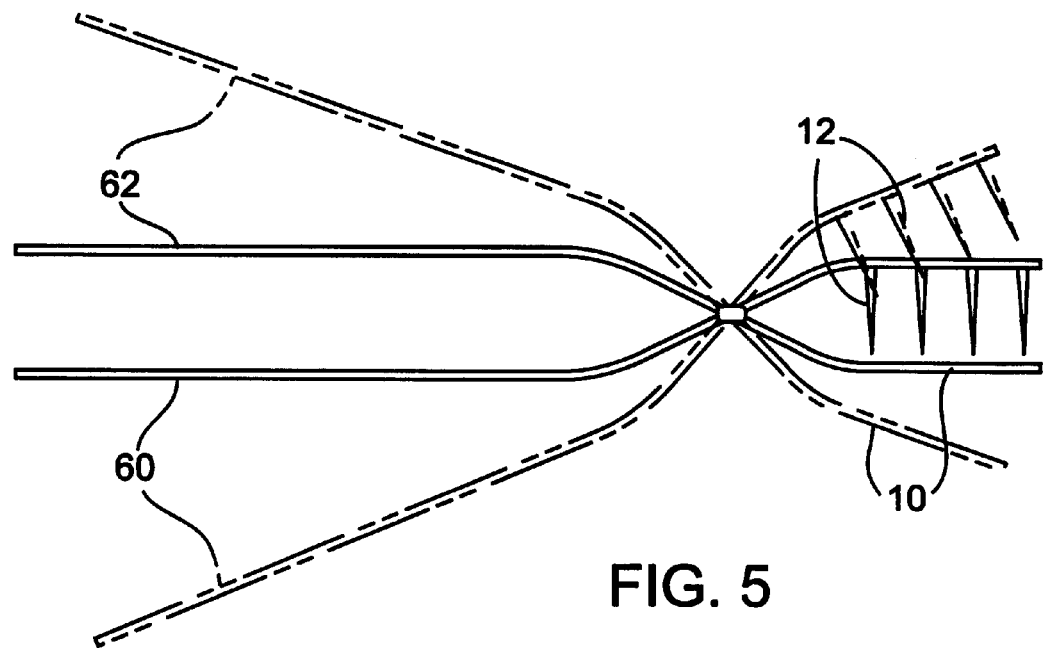
FIG. 5 illustrates a scissors-type actuating mechanism that can be used with the jaws of FIG. 1.
Figure 6:
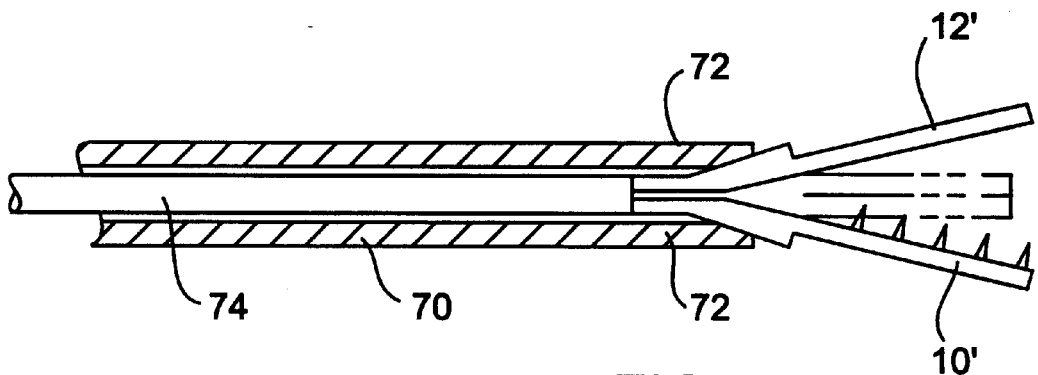
FIG. 6 illustrates a pair of resiliently-mounted jaws that can be opened and closed with a cam surface, where the jaws incorporate tissue-penetrating elements according to the principles of the present invention.
Figure 7:
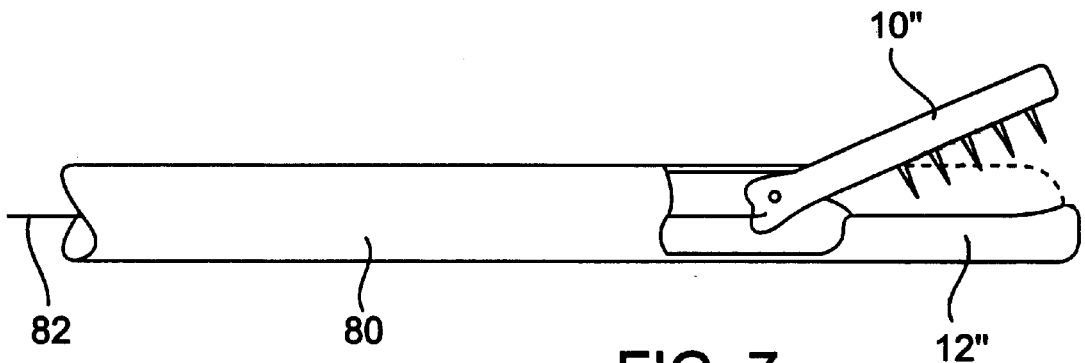
FIG. 7 illustrates an alternative jaw actuating mechanism which may be utilized in the devices of the present invention.

Referring now to FIGS. 5–7, the present invention can rely on virtually any jaw-actuating mechanism of a type utilized in medical devices. For example, the mechanism can be a simple scissors mechanism, as shown in FIG. 5, where the jaws 10 and 12 are pivotally connected to actuating levers 60 and 62. Opening and closing of the levers 60 and 62 will open and close the jaws in a conventional manner.

Jaws 10' and 12' can also be mounted within a hollow tube 70 having cam surfaces 72 formed at its distal end. The jaws 10' and 12' are resiliently mounted on a rod 74 so that the jaws may be axially translated relative to the cam surfaces 72 to open the jaws (as shown in full line) and close the jaws (as shown in broken line) in FIG. 6.

As a third common alternative, jaws 10" and 12" may be formed at the distal end of a tubular actuator 80. The jaw 10" which is free from tissue penetrating elements is integrally formed at the end of the tube 80. The moveable jaw 10" having the tissue penetrating elements is pivotally attached and is actuated by a rod 74 or cable 82 extending to a proximal end of the device (not shown).

The assemblies of FIGS. 6 and 7 may be manually operated by conventional proximal assemblies (not shown), such as three-ring actuators, pistol grips, or any other actuator which permits linear movement of the rod 74 or cable 82. The devices of FIGS. 6 and 7 would be particularly useful for laparoscopic, thoracoscopic, arthroscopic, or other procedures where they are to be introduced through narrow diameter cannulas, typically having shaft diameters below 12 mm, more typically below 10 mm, and sometimes 5 mm or smaller.

Figure 1B:
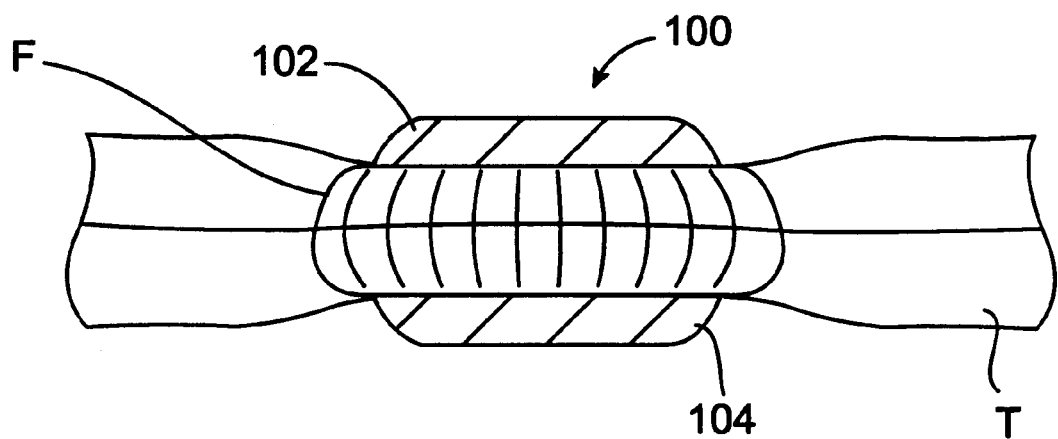
Figure 8:
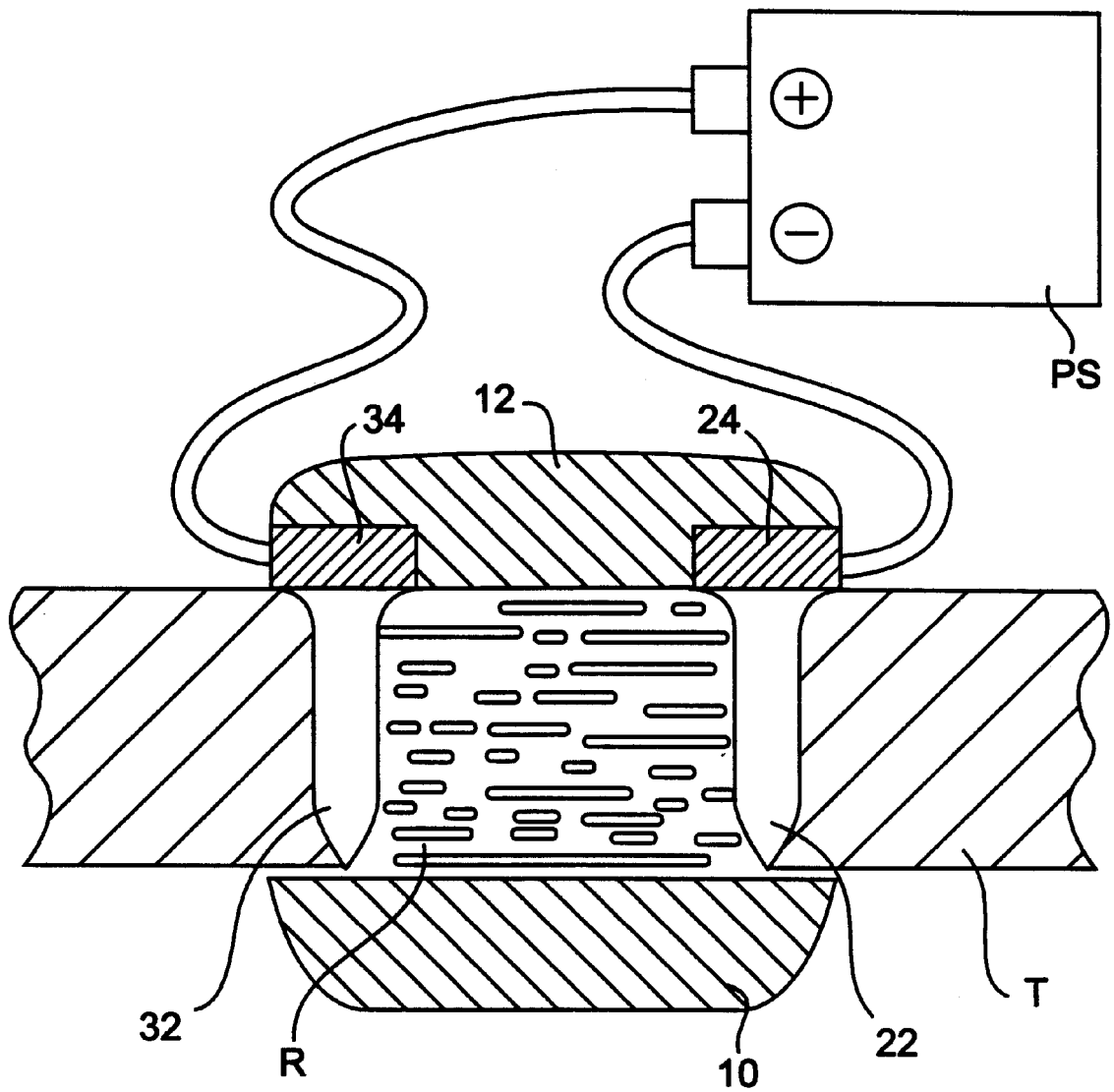
FIG. 8 illustrates use of the jaws of FIG. 1 in treating tissue according to the method of the present invention.

Referring now to FIG. 8, use of the jaws 10 and 12 of FIGS. 1–3 for treating tissue T is illustrated. The jaws 10 and 12 are actuated to grasp a tissue structure, such as an artery, vein, fallopian tube, ligament, or other tubular or elongate structure therebetween. The tissue penetrating elements 22 and 32 pierce and penetrate into the tissue T to create a region R therebetween. The electrically conductive strips 24 and 34 are attached to an external power supply PS so that they may be energized with opposite polarities. Suitable power supplies are available from commercial suppliers, such as Valleylab, Aspen, and Bovie. The power supplies may operate with conventional sinusoidal or non-sinusoidal wave forms and may operate at fixed or controlled power levels, where voltage, current, or both may be selected. When energized at the power levels, frequencies, and durations described above, the tissue region R between the lines of penetrating elements 22 and 32 will receive a high flux of energy, causing heating, coagulation, and optionally necrosis of the tissue. Heating of the adjacent tissues outside of this region R is minimal.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A bipolar surgical instrument comprising:
    a shaft having a proximal end and a distal end;
    a pair of opposed jaws at the distal end of the shaft;
    a first electrode member on one of the jaws;
    a second electrode member on one of the jaws, wherein the first and second electrode members are electrically isolated from each other; and
    an actuating mechanism for moving the jaws between an opened and closed configuration, wherein electrode members lie parallel to and laterally spaced-apart from each other when the jaws are closed, wherein at least one of the electrode members comprises a plurality of tissue penetrating elements which project toward the opposed jaw.

2. A bipolar surgical instrument as in claim 1, wherein the electrode members are laterally spaced-apart by a distance in the range from 0.5 mm to 10 mm.

3. A bipolar surgical instrument as in claim 1, wherein the electrode members have a length in the range from 5 mm to 30 mm and a width from 0.5 mm to 5 mm.

4. A bipolar surgical instrument as in claim 1, wherein electrode members are on the same jaw.

5. A bipolar surgical instrument as in claim 1, wherein the first electrode member is on one jaw and the second electrode member is on the other jaw.

6. A bipolar surgical instrument as in claim 1, wherein both electrode members comprise a plurality of tissue penetrating elements which project toward the opposed jaw.

7. A bipolar surgical instrument as in claim 1, wherein the tissue penetrating elements have a length in the range from 1 mm to 6 mm and a diameter in the range from 0.1 mm to 1 mm.

8. A bipolar surgical instrument as in claim 6, wherein the first and second electrode members each comprise from 5 to 20 tissue penetrating elements.

9. A bipolar surgical instrument as in claim 8, wherein the tissue-penetrating elements are arranged in two straight lines which are parallel to each other when the jaws are closed over tissue.

10. A bipolar surgical instrument as in claim 1, further comprising a third electrode member aligned with the first electrode member but disposed on the other jaw and a fourth electrode member aligned with the second electrode member but disposed on the other jaw.

11. A bipolar surgical instrument as in claim 1, wherein at least one of the jaws is perforated to permit the release of steam during use.

12. A bipolar surgical instrument as in claim 1, wherein the actuating mechanism comprises scissors, a camming mechanism, or a linear/pivot actuator.

13. A method for applying high frequency electrical energy to tissue, said method comprising:
    grasping tissue between first jaw and a second jaw;
    applying high frequency energy between a first electrode member comprising a first line of tissue-penetrating elements on one of said jaws and a second electrode member comprising a second line of tissue-penetrating elements on one of said jaws, wherein said lines of tissue penetrating elements are parallel to and laterally spaced-apart from each other when grasping the tissue.

14. A method as in claim 13, wherein the high frequency energy is applied at a level and for a time sufficient to necrose substantially all tissue between said electrode members without causing substantial damage to other tissue.

15. A method as in claim 14, wherein the high frequency energy has a frequency from 100 kHz to 1 MHz, a power level from 25 W to 200 W, and is applied for a time from 5 seconds to 5 minutes.

16. A method as in claim 13, wherein the electrode members are laterally spaced-apart by a distance in the range from 0.5 mm to 10 mm.

17. A method as in claim 13, wherein the electrode members have a length in the range from 5 mm to 30 mm and a width from 0.5 mm to 5 mm.

18. A method as in claim 13, wherein both electrode members are on the same jaw.

19. A method as in claim 13, wherein the first electrode member is on one jaw and the second electrode member is on the other jaw.

20. A method as in claim 13, wherein at least one of the electrode members comprises a plurality of tissue penetrating elements which project toward the opposed jaw.

21. A method as in claim 19, wherein the tissue penetrating elements have a length from 1 mm to 6 mm and a diameter in the range from 0.1 mm to 1 mm.

22. A method as in claims 21, wherein the first and second electrode members each comprise from 5 to 20 tissue-penetrating elements.

23. A method as in claims 20, wherein the tissue penetrating elements are arranged in two straight lines which are parallel to each other when the jaws are closed over the tissue.

24. A methods as in claim 20, wherein the energy is further applied between a third electrode member aligned with the first electrode member but disposed on the other jaw and a fourth electrode member aligned with the second electrode member but disposed on the other jaw.

25. A method as in claim 13, wherein at least one of the jaws is perforated to permit the release of steam during use.

26. A bipolar surgical instrument comprising:
    a shaft having a proximal end and a distal end;
    a pair of opposed jaws at the distal end of the shaft;
    a first electrode member on one of the jaws;
    a second electrode member on one of the jaws, wherein the first and second electrode members are electrically isolated from each other;
    a third electrode member aligned with the first electrode member but disposed on the other jaw and a fourth electrode member aligned with the second electrode member but disposed on the other jaw; and
    an actuating mechanism for moving the jaws between an opened and closed configuration, wherein electrode members lie parallel to and laterally spaced-apart from each other when the jaws are closed.

27. A bipolar surgical instrument as in claim 26, wherein the electrode members are laterally spaced-apart by a distance in the range from 0.5 mm to 10 mm.

28. A bipolar surgical instrument as in claim 26, wherein the electrode members have a length in the range from 5 mm to 30 mm and a width from 0.5 mm to 5 mm.

29. A bipolar surgical instrument as in claim 26, wherein electrode members are on the same jaw.

30. A bipolar surgical instrument as in claim 26, wherein the first electrode member is on one jaw and the second electrode member is on the other jaw.

31. A bipolar surgical instrument as in claim 26, wherein at least one of the electrode members comprises a plurality of tissue penetrating elements which project toward the opposed jaw.

32. A bipolar surgical instrument as in claim 26, wherein both electrode members comprise a plurality of tissue penetrating elements which project toward the opposed jaw.

33. A bipolar surgical instrument as in claim 31, wherein the tissue penetrating elements have a length in the range from 1 mm to 6 mm and a diameter in the range from 0.1 mm to 1 mm.

34. A bipolar surgical instrument as in claim 32, wherein the first and second electrode members each comprise from 5 to 20 tissue-penetrating elements.

35. A bipolar surgical instrument as in claim 34, wherein the tissue-penetrating elements are arranged in two straight lines which are parallel to each other when the jaws are closed over tissue.

36. A bipolar surgical instrument as in claim 26, wherein at least one of the jaws is perforated to permit the release of steam during use.

37. A bipolar surgical instrument as in claim 26, wherein the actuating mechanism comprises scissors, a camming mechanism, or a linear/pivot actuator.

38. A bipolar surgical instrument comprising:
   a shaft having a proximal end and a distal end;
   a pair of opposed jaws at the distal end of the shaft;
   a first electrode member on one of the jaws;
   a second electrode member on one of the jaws, wherein the first and second electrode members are electrically isolated from each other;
   wherein at least one of the jaws is perforated to permit the release of steam during use; and
   an actuating mechanism for moving the jaws between an opened and closed configuration, wherein electrode members lie parallel to and laterally spaced-apart from each other when the jaws are closed.

39. A bipolar surgical instrument as in claim 38, wherein the electrode members are laterally spaced-apart by a distance in the range from 0.5 mm to 10 mm.

40. A bipolar surgical instrument as in claim 38, wherein the electrode members have a length in the range from 5 mm to 30 mm and a width from 0.5 mm to 5 mm.

41. A bipolar surgical instrument as in claim 38, wherein electrode members are on the same jaw.

42. A bipolar surgical instrument as in claim 38, wherein the first electrode member is on one jaw and the second electrode member is on the other jaw.

43. A bipolar surgical instrument as in claim 38, wherein at least one of the electrode members comprises a plurality of tissue penetrating elements which project toward the opposed jaw.

44. A bipolar surgical instrument as in claim 38, wherein both electrode members comprise a plurality of tissue penetrating elements which project toward the opposed jaw.

45. A bipolar surgical instrument as in claim 43, wherein the tissue penetrating elements have a length in the range from 1 mm to 6 mm and a diameter in the range from 0.1 mm to 1 mm.

46. A bipolar surgical instrument as in claim 44, wherein the first and second electrode members each comprise from 5 to 20 tissue-penetrating elements.

47. A bipolar surgical instrument as in claim 46, wherein the tissue-penetrating elements are arranged in two straight lines which are parallel to each other when the jaws are closed over tissue.

48. A bipolar surgical instrument as in claim 38, further comprising a third electrode member aligned with the first electrode member but disposed on the other jaw and a fourth electrode member aligned with the second electrode member but disposed on the other jaw.

49. A bipolar surgical instrument as in claim 38, wherein the actuating mechanism comprises scissors, a camming mechanism, or a linear/pivot actuator.

* * * * *